(12) United States Patent
Su et al.

(10) Patent No.: US 8,545,773 B2
(45) Date of Patent: Oct. 1, 2013

(54) VERSATILE MULTICHANNEL CAPILLARY BIOSENSOR SYSTEM

(75) Inventors: Xiao-Li Su, Fayetteville, AR (US); Zungzhong Ye, Hangzhou (CN); Qian Sun, Fayetteville, AR (US); Yanbin Li, Fayetteville, AR (US)

(73) Assignees: The Board of Trustees of the University of Arkansas, Little Rock, AR (US); BioDetection Instruments, LLC, Fayetteville, AR (US)

( * ) Notice: Subject to any disclaimer, the term of this patent is extended or adjusted under 35 U.S.C. 154(b) by 467 days.

(21) Appl. No.: 12/670,467

(22) PCT Filed: Jul. 24, 2008

(86) PCT No.: PCT/US2008/008971
§ 371 (c)(1),
(2), (4) Date: Jul. 7, 2010

(87) PCT Pub. No.: WO2009/014725
PCT Pub. Date: Jan. 29, 2009

(65) Prior Publication Data
US 2010/0285522 A1    Nov. 11, 2010

Related U.S. Application Data

(60) Provisional application No. 60/961,965, filed on Jul. 25, 2007.

(51) Int. Cl.
*B01L 99/00* (2010.01)
(52) U.S. Cl.
USPC ............ 422/537; 422/63; 422/64; 422/65; 422/66; 422/67; 422/50; 422/500; 422/501; 422/502

(58) Field of Classification Search
USPC ............... 422/50, 63–67, 500–502, 537
See application file for complete search history.

(56) References Cited

U.S. PATENT DOCUMENTS

| | | | | |
|---|---|---|---|---|
| 4,913,821 A | * | 4/1990 | Melcher et al. | 210/635 |
| 6,012,487 A | * | 1/2000 | Hauck | 137/625.11 |
| 2007/0074972 A1 | * | 4/2007 | Nassef et al. | 204/451 |

OTHER PUBLICATIONS

Su, X., Q. Sun, Z. Ye and Y. Li. 2006. A prototype capillary biosensor for foodborne pathogens detection. Presented at PITTCON 2006 Annual Meeting, Mar. 12-17, Orlando, FL. Poster # 2140-6P.
Sun, Q., X. Su, J. Millett and Y. Li. 2006. A capillary-based immunosensor for rapid detection of atrazine residue. Presented at IFT 2006 Annual Meeting, Jun. 24-28, 2006, Orlando, FL.

(Continued)

*Primary Examiner* — Jyoti Nagpaul
(74) *Attorney, Agent, or Firm* — J. Charles Dougherty

(57) ABSTRACT

The multichannel capillary biosensor system includes a selecting valve system for selection of the sample or a reagent. The selecting valve system is connected to a second valve system accommodating a sensing channel and a first bypass channel. The second valve system is connected to a directing valve system having at least two positions, with a first position being connected to a second bypass channel and a second position being connected to a detector for detecting the analyte. The device has a pump connected at one end to the second bypass channel and the detector and at a second end to a waste vessel. The device also has a control system for controlling the device. The analyte can be selected from the group of microorganisms, macromolecules, and small molecules.

14 Claims, 14 Drawing Sheets

(56) References Cited

OTHER PUBLICATIONS

Ye, Z., Y. Li, Y. Ying, X. Su and Q. Sun. 2006. Design, construction and evaluation of a portable biosensor for rapid detection of *E. coli* O157:H7. Presented at ASABE 2006 Annual Meeting, Jul. 9-12, 2006, Portland, OR. ASABE Paper No. 067121.

Su, X., Q. Sun, B. Kim and Y. Li. 2005. An automatic capillary immunoassay system for detection of foodborne pathogens. Presented at ASAE 2005 Annual Meeting, Jul. 17-20, Tampa, FL. ASAE Paper No. 057026.

Liu, Y. and Li, Y. 2001. An antibody-immobilized capillary column as a bioseparator/bioreactor for detection of *E. coli* O157:H7 with absorbance measurement. Anal. Chem. 73 (21): 5180-5183.

Kim, B., X.-L. Su, and Y. Li. 2005. Evaluation of a capillary immunoassay system for detection of *Salmonella typhimurium* in poultry products, J. Food Prot. 68 (9): 1799-1803.

Li, Y. and X.-L. Su. 2006. Microfluidics-based optical biosensing method for rapid detection of *Escherichia coli* O157: H7, J. Rapid Meth. Automat. Microbiol., 14, 96-109.

Office communication dated Feb. 18, 2010 for co-pending U.S. Appl. No. 10/425,510.
Examiner's Answer dated Sep. 2, 2009 for co-pending U.S. Appl. No. 10/425,510.
Office communication dated Dec. 11, 2008 for co-pending U.S. Appl. No. 10/425,510.
Office communication dated Sep. 18, 2008 for co-pending U.S. Appl. No. 10/425,510.
Office communication dated Jun. 18, 2008 for co-pending U.S. Appl. No. 10/425,510.
Office communication dated Jan. 11, 2008 for co-pending U.S. Appl. No. 10/425,510.
Office communication dated Jun. 28, 2007 for co-pending U.S. Appl. No. 10/425,510.
Office communication dated Jan. 24, 2007 for co-pending U.S. Appl. No. 10/425,510.
Office communication dated Aug. 8, 2006 for co-pending U.S. Appl. No. 10/425,510.
Office communication dated Apr. 28, 2005 for co-pending U.S. Appl. No. 10/425,510.

* cited by examiner

VERSATILE MULTICHANNEL CAPILLARY BIOSENSOR SYSTEM

REFERENCE TO RELATED APPLICATIONS

This application is the U.S. National Stage of International Application No. PCT/US2008/008971, filed 24 Jul. 2008, which claims the benefit of U.S. Provisional Application No. 60/961,965, filed 25 Jul. 2007, both of which are incorporated herein by reference.

STATEMENT REGARDING FEDERALLY SPONSORED RESEARCH OR DEVELOPMENT

This invention was made with Government support under the terms of Grant Nos. NSF 0422088, NSF 0512668, and NIH 2R44RR018420-02. The Government has certain rights in the invention.

TECHNICAL FIELD OF THE INVENTION

This invention generally relates to a device for detecting an analyte in a sample.

BACKGROUND

A multichannel biosensor instrument for rapid, specific, and sensitive detection of microorganisms, macromolecules, and small molecules is described. It uses highly efficient capillary bioseparators/bioreactors to specifically capture and separate target biological and/or chemical agents (including bacteria, viruses, proteins, toxins, pesticides, antibiotics, etc.) from food, environmental, or clinical samples and to quickly generate quantitative optical signals. The applications of the biosensor system include, but are not limited to, rapid detection of food pathogens, protein biomarkers, and pesticide residues.

Microbial contamination of food products by pathogenic bacteria remains a major concern of our society. Contaminated food is estimated to cause 76 million illnesses, with 325,000 serious illnesses resulting in hospitalization, and 5,000 deaths in the United States each year. Although conventional culture methods hypothetically allow the detection of a single cell of specific pathogens, these methods are extremely time-consuming, typically requiring at least 24 h and involve complicated multi-steps to confirm the analysis. Even current rapid methods such as ELISA and PCR still require enrichment of samples for 8-24 h and take several hours to get only qualitative (positive/negative) results. These methods also require elaborate laboratory setup and highly skilled personnel. Since current food processing and distribution systems operate at a very high speed and the infectious dosage of some foodborne pathogens are very low, it is extremely important to develop new, rapid yet sensitive methods for the detection of pathogens in food products. This is a critical step in ensuring the safety of the food supply.

As we move into the post-genomic era, there is an increasing need to identify specific proteins and investigate the relationships between protein expressions and specific cellular processes. Western blot analysis and two-dimensional gel electrophoresis (2-DE) followed by matrix assisted laser desorption ionization/time of flight (MALDI/TOF) mass spectrometry (MS) analysis are both powerful tools in proteomics research. The 96- or 384-well ELISA, immunobeads based flow cytometry, protein microarrays, etc. are also frequently used for high-throughput protein detection. However, many problems still plague these methods including the requirement of expensive or large equipment (e.g., 2-DE MALDI/TOF MS), extensive sample pretreatment (e.g. flow cytometry), intensive manual operations (e.g. ELISA), highly skilled personnel, or lack of appropriate sensitivity (e.g. protein microarray).

The potential hazard of pesticides makes it vital to monitor residues in drinking water, the food supply, and the environment. HPLC and GC are standard methods for detection of pesticide residues. These methods are reliable and have adequate sensitivity or detection limits required by the regulatory standards. However, these methods require extensive sample preparation and pre-concentration as well as expensive instrumentation and skilled personnel.

DETAILED DESCRIPTION

Because of the potential advantages in the ease-of-use and cost-effectiveness, biosensors are an alternative technology for rapid detection of microorganisms, macromolecules, and small molecules. Among the biosensor methods, immunosensors provide the highest specificity and versatility. Therefore, an immunosensing technology is employed in the presented biosensor system.

This biosensor instrument has a unique system configuration with analytical procedures that enhance detection sensitivity, reduce detection time, eliminate cross-contamination, and lower operation cost, which make analytical applications both practical and reliable. It is based on unique, highly efficient capillary bioseparators/bioreactors that specifically capture and separate target microorganisms, macromolecules, and/or small molecules from a variety of sample matrices (including but not limited to food, environmental, clinical samples). It can quickly generate quantitative optical signals. The instrument is capable of detecting various analytes, including microorganisms, macromolecules, and small molecules from the sample matrices listed above. Examples of microorganisms that have been detected include *E. coli* O157:H7, *Salmonella Typhimurium*, and *Listeria monocytogenes*. Examples of macromolecules that have been detected include vinculin and cytochrome c. Examples of small molecules that have been detected includes the pesticide atrazine.

The biosensor system has been successfully applied to detect pathogenic bacteria including *E. coli* O157:H7, *Salmonella Typhimurium, Listeria monocytogenes* in meat, poultry samples, ready to eat milk, lettuce and beef lunchmeat samples, protein biomarkers including vinculin and cytochrome c in chickens, and atrazine, one of the most used pesticides, in water, milk and apple juice samples with a total analysis time of approximately 2 h (or less than 1 h depending on the target of the detection) per 5 samples and a lowest detection limit of 100-1000 cfu/mL, 40 pM, and 1 ng/mL (1 ppb), respectively. The detection limits achieved were approximately 10-100 times lower than those obtained with conventional ELISA methods without sacrificing the inherent specificity of immunoassays. The relative standard deviations were generally less than 10%.

System Configuration

Figure 1:
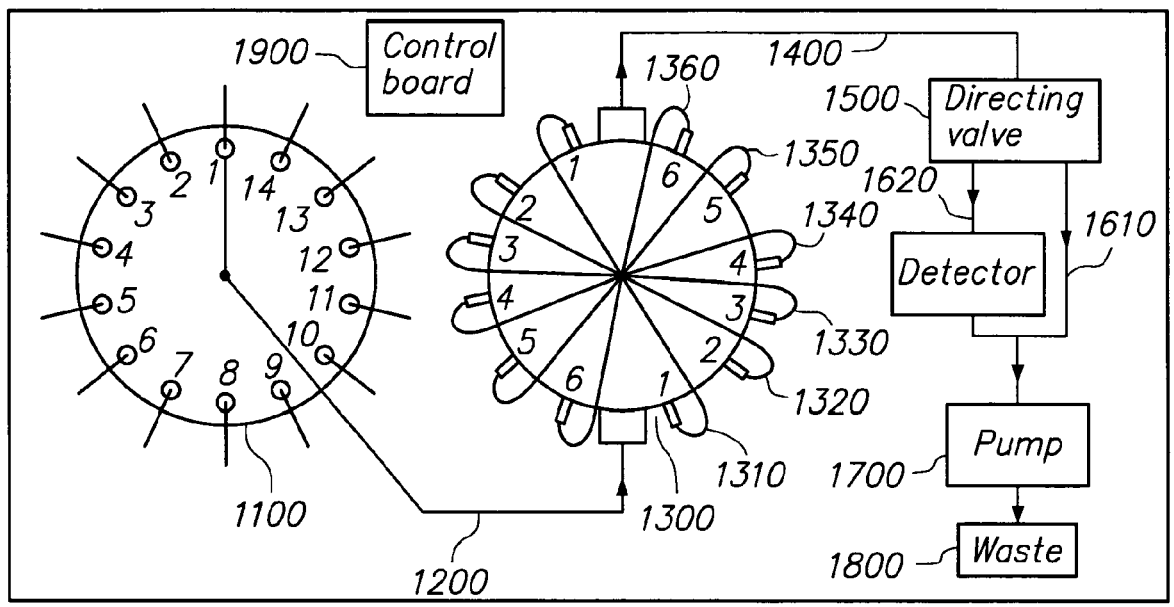
FIG. 1. Schematic diagram showing a preferred configuration of the multichannel biosensor system. 1100, multi-position valve; 1200, connecting tubing 1; 1300, multi-channel valve; 1310, bypass 1; 1320-1360, sensing channels; 1400, connecting tubing 2; 1500, directing valve; 1610, bypass 2; 1620, detector; 1700, pump; 1800, waste vessel; 1900, control board.
Figure 2:
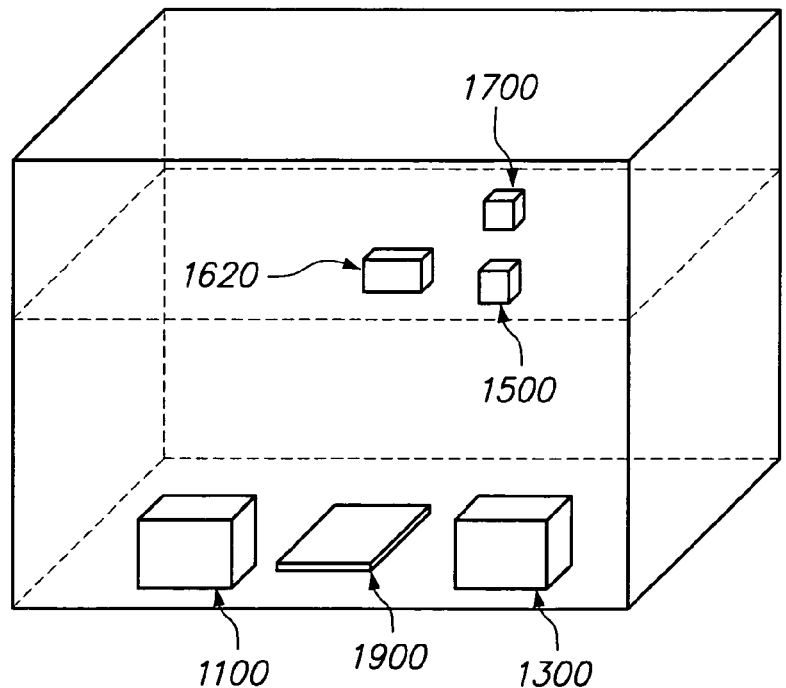
FIG. 2. Simplified drawing showing locations of individual components of the biosensor system. 1100, multi-position valve; 1300, multi-channel valve; 1500, directing valve; 1620, detector; 1700, pump; 1900, control board.
Figure 3:
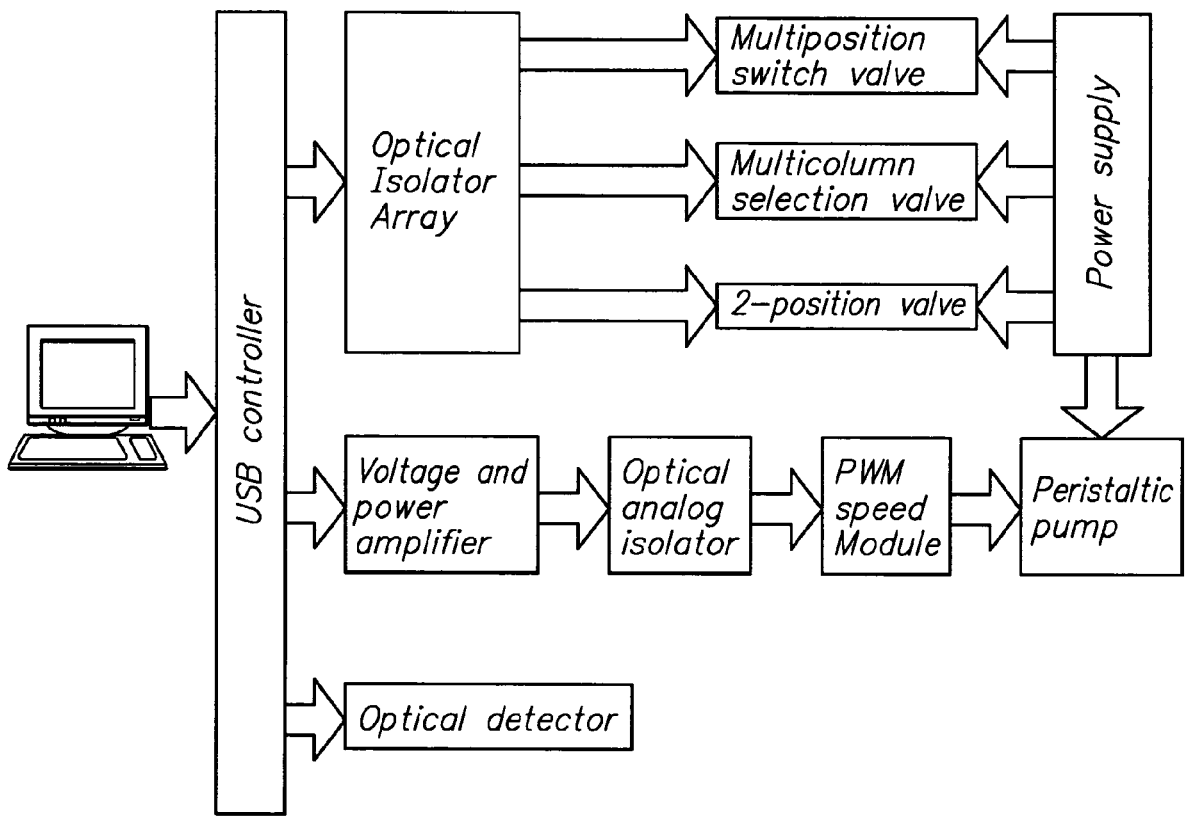
FIG. 3. Schematic diagram of electric control circuit of the multichannel biosensor system.
Figure 4:
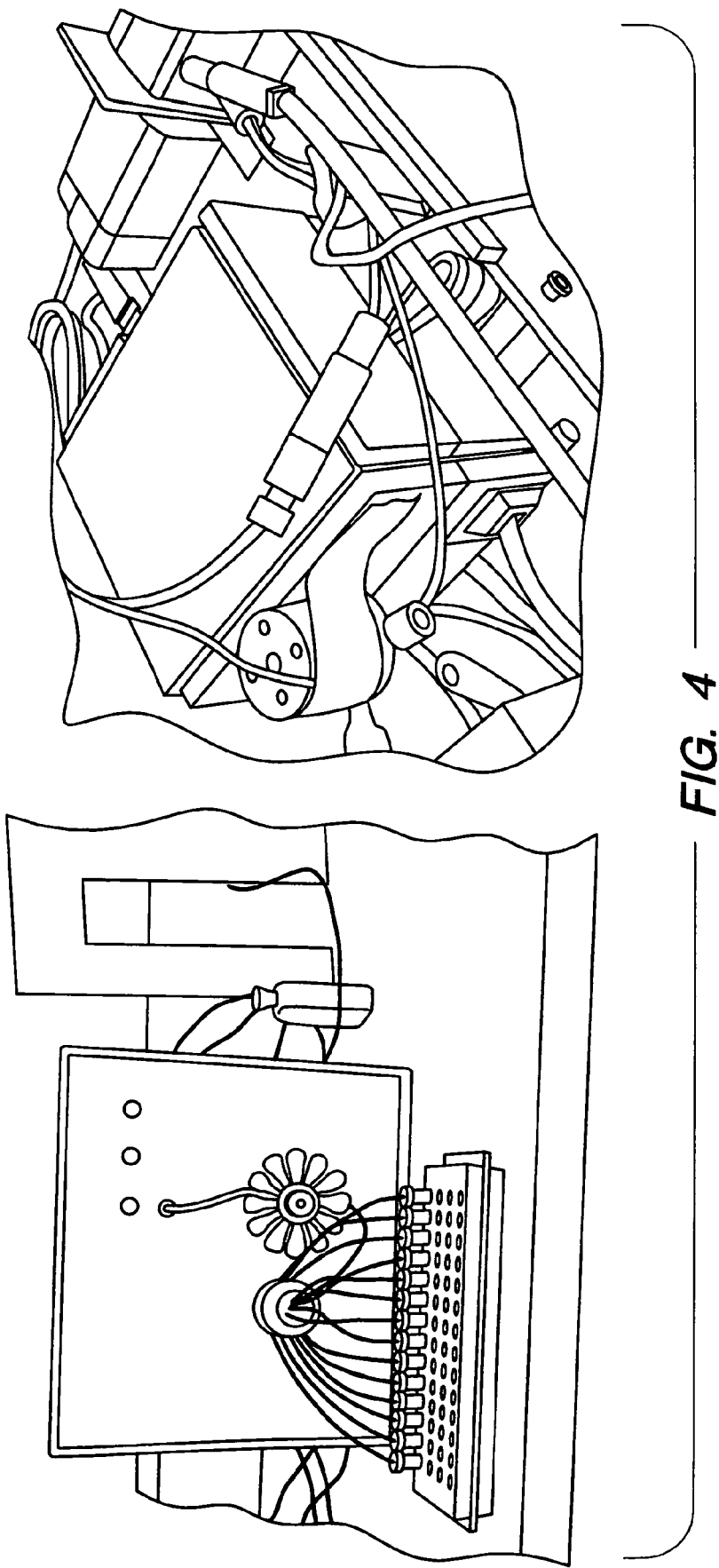
FIG. 4. The external (left) and internal (right) views of the multichannel biosensor system.

As shown in FIG. 1, the biosensor system for detection of an analyte in a sample comprises: a selecting valve system for selection of the sample or a reagent connected to a second valve system accommodating at least one sensing channel and a first bypass channel; the second valve system being connected to a directing valve system having at least two positions, with a first position being connected to a second bypass channel and a second position being connected to a detector for detecting the analyte; a pump connected at one end to the second bypass channel and the detector and at a second end to a waste vessel; and a control system for controlling the device. FIG. 2 shows a simplified drawing of locations of individual components of the biosensor system. FIG. 3 shows the electric control circuit schematic diagram of a preferred biosensor system. The external and internal views of the biosensor system are shown in FIG. 4.

A peristaltic pump-based biosensor system has been compared with syringe pump-based and solenoid pump-based systems. Both syringe pumps and solenoid pumps have some limitations. Although syringe pumps can control sample/reagent volume and flow rate precisely and accurately, they are large in size, expensive, and only capable of offering continuous flow of a limited volume that is determined by the syringe size. Although solenoid micropumps are suitable for shrinking the whole biosensor system, their strokes are so violent that it frequently draws air and causes a bubble problem, which can interfere with the measurement of optical absorbance. The peristaltic pump-based system is the best among the three systems because the pump used is the cheapest, has a small size comparable to the solenoid micropump, is capable of controlling sample/reagent volume and flow rate with precision and accuracy comparable to the syringe pump, and can offer a continuous flow of a large volume, which is particularly useful for washing purpose.

Software

Figure 5:
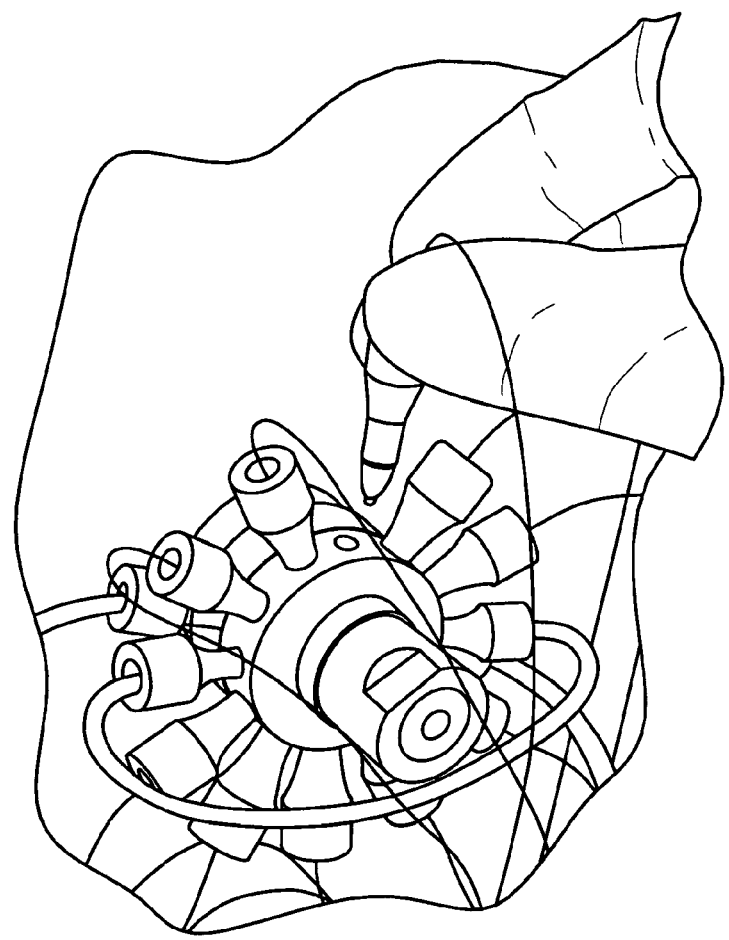
FIG. 5. Installation of capillary columns.
Figure 5:

The biosensor system is highly automated via the control of a laptop PC with the aid of the software written in Visual Basic. To start a new test, the user only needs to install capillary columns (FIG. 5) into the instrument and load reagents/samples into the reservoirs, which can be done in a couple of minutes, and to simply click the "Run" button on the control panel. A defined sample analysis cycle is automatically executed by the instrument, and the instrument signal is displayed on the screen in real time as a dynamic graph, which is saved automatically when the test cycle is completed.

Figure 6:
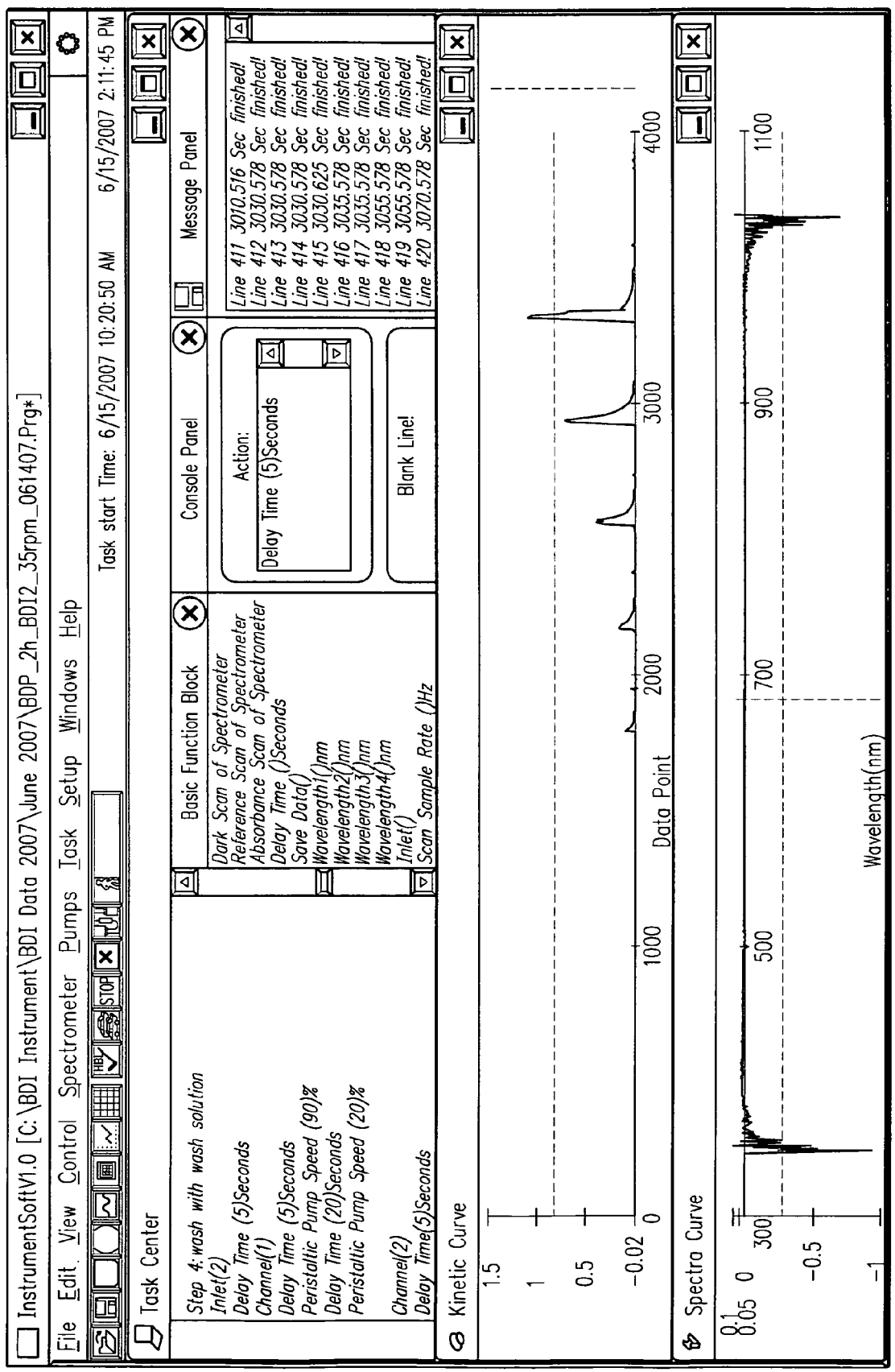
FIG. 6. Software for the multichannel biosensor system.
Figure 7:
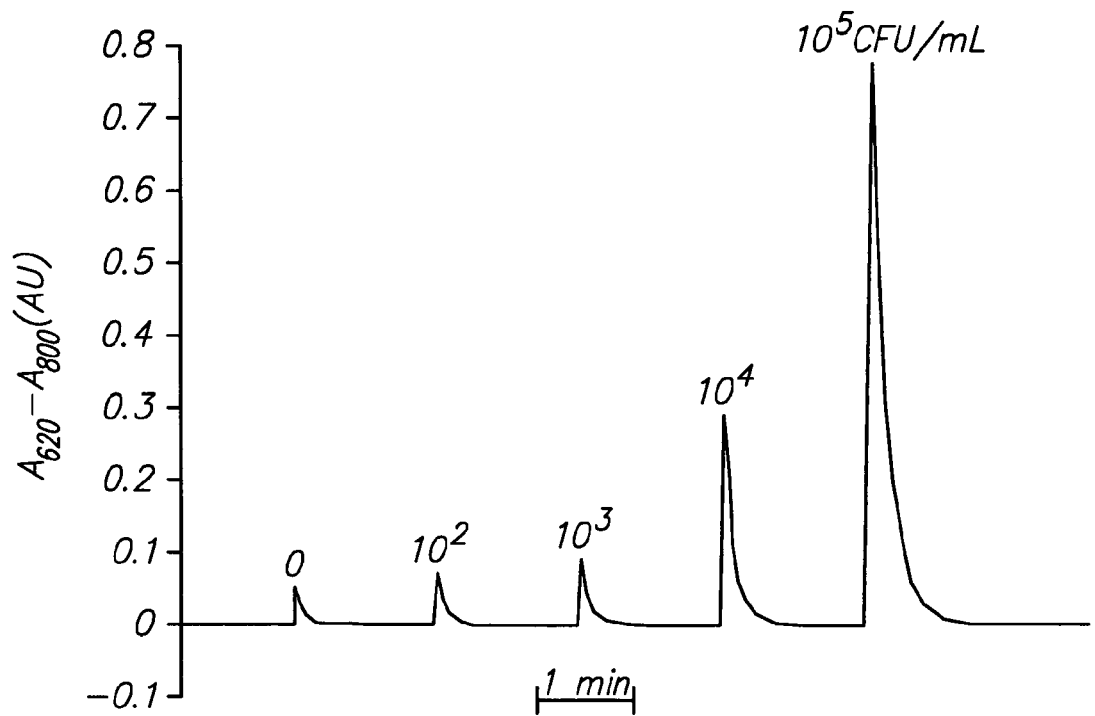
FIG. 7. Result of the biosensor system for the detection of *E. coli* O157:H7 in PBS showing a detection limit of ~$10^2$ cfu/mL without enrichment.
Figure 8:
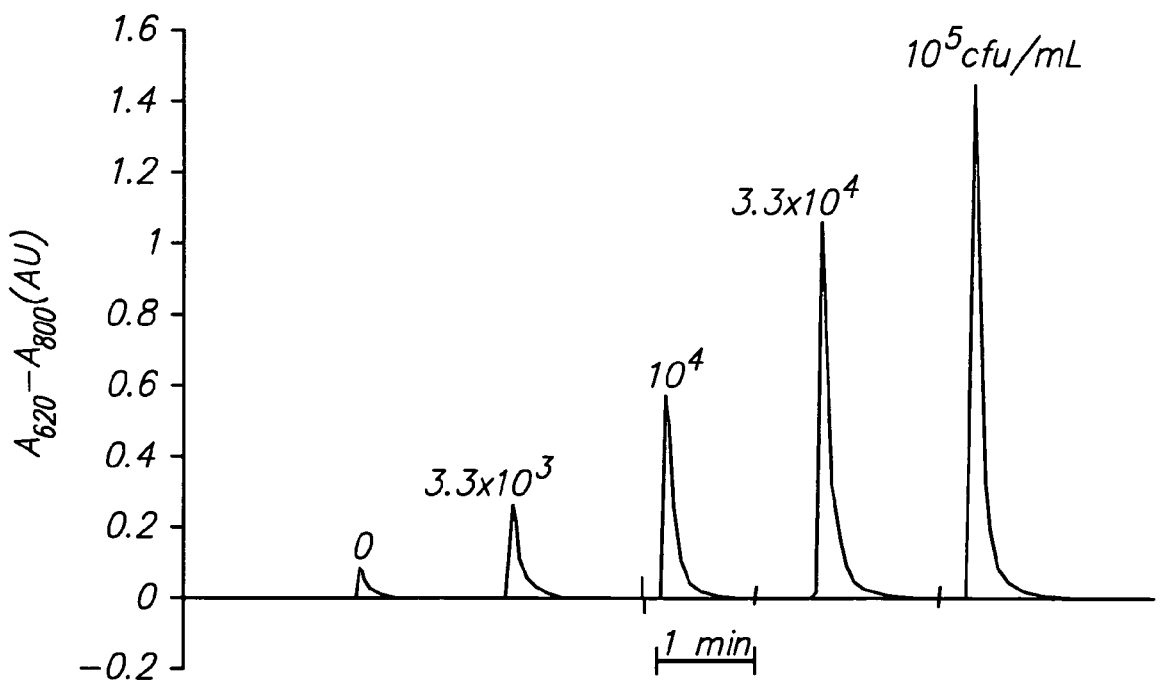
FIG. 8. Result of the biosensor system for quantitation of *E. coli* O157:H7 in PBS without enrichment.
Figure 9:
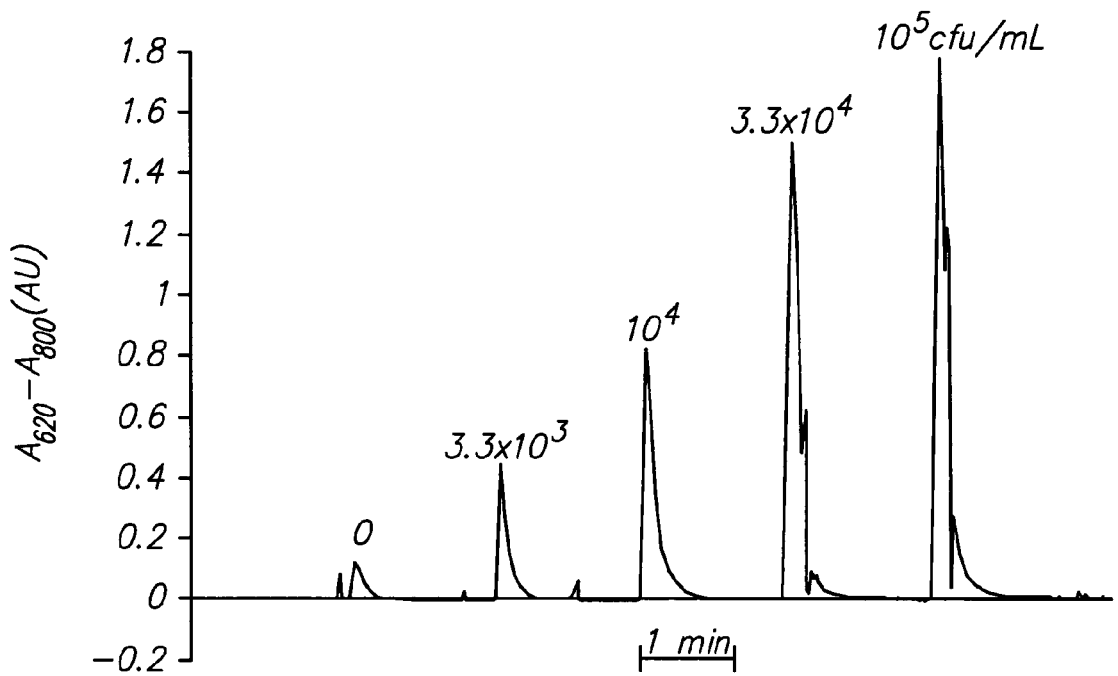
FIG. 9. Result of the biosensor system for quantitation of *E. coli* O157:H7 in inoculated ready-to-eat beef lunchmeat.
Figure 10:
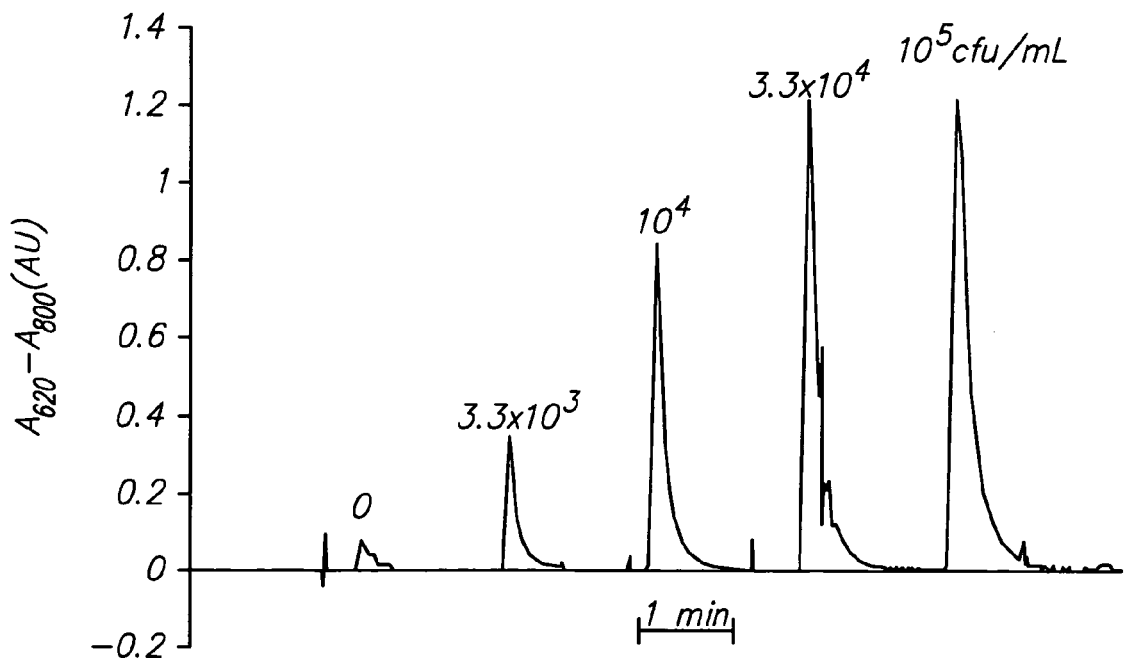
FIG. 10. Result of the biosensor system for quantitation of *E. coli* O157:H7 in inoculated ready-to-eat lettuce without enrichment.
Figure 11:
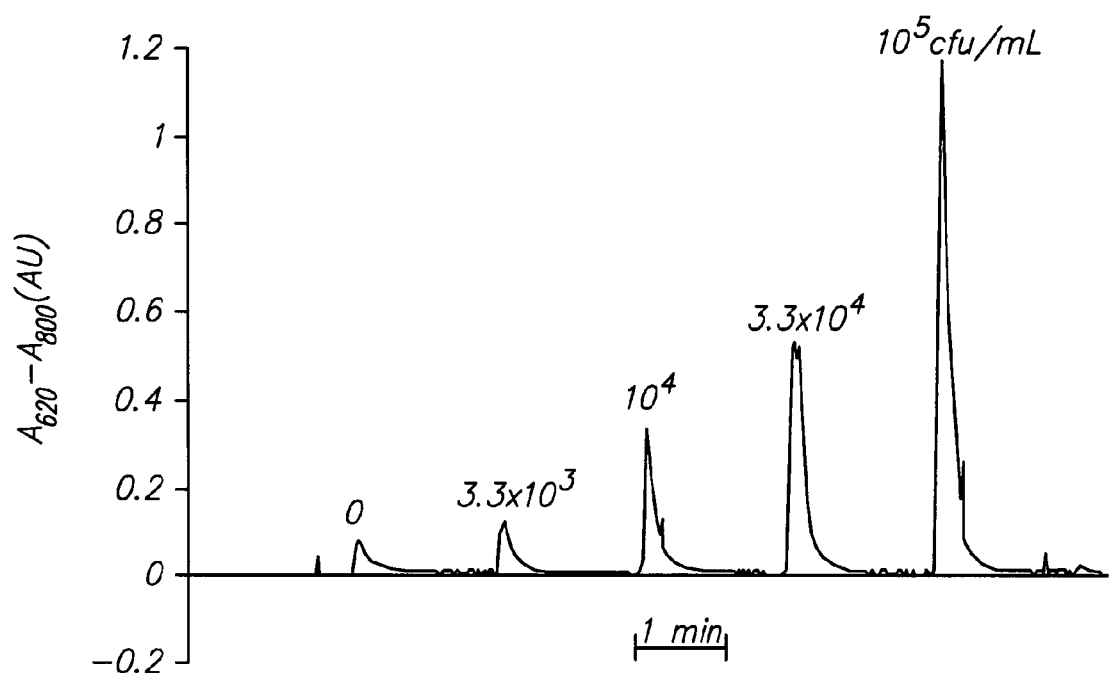
FIG. 11. Result of the biosensor system for quantitation of *E. coli* O157:H7 in inoculated milk.
Figure 12:
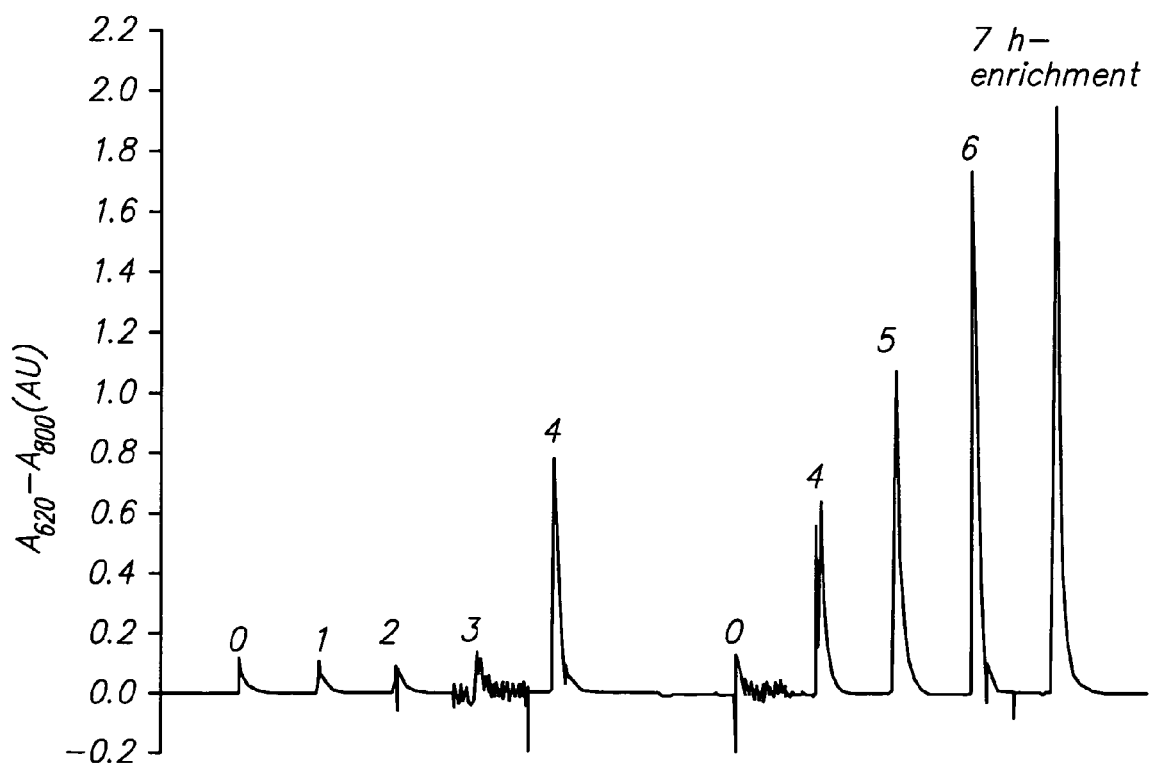
FIG. 12. Result of enrichment test showing that the biosensor system can detect <10 cfu/mL of *E. coli* O157:H7 in buffer with ~4 h enrichment.
Figure 13:
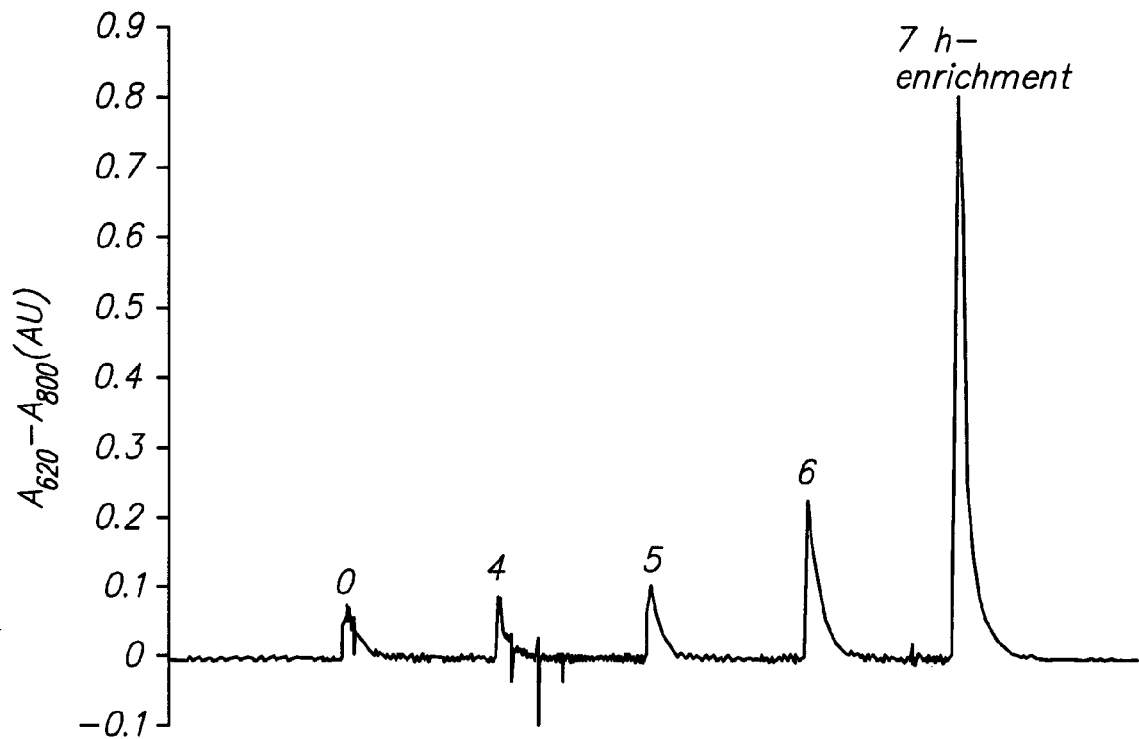
FIG. 13. Result of enrichment test showing that the biosensor system can detect <1 cfu/mL of *E. coli* O157:H7 in spiked ready-to-eat lettuce with ~6 h enrichment.
Figure 14:
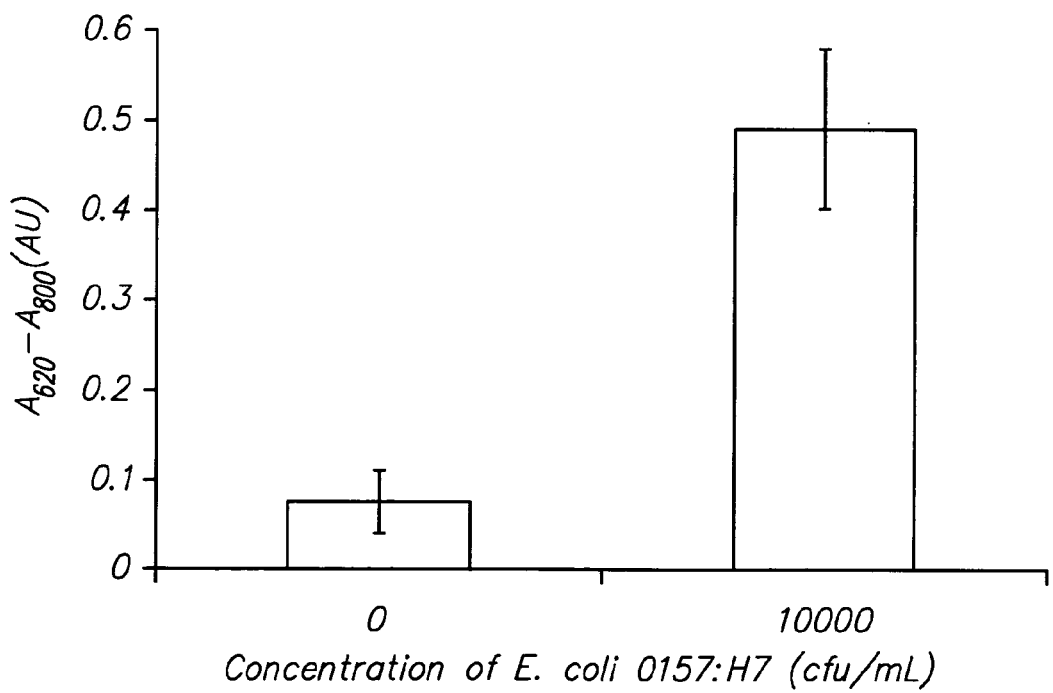
FIG. 14. Result of reproducibility test for the detection of *E. coli* O157:H7 in PBS without enrichment. Number of blanks: 2/test×5 tests=10; Number of samples: 3/test×5 tests=15.
Figure 15:
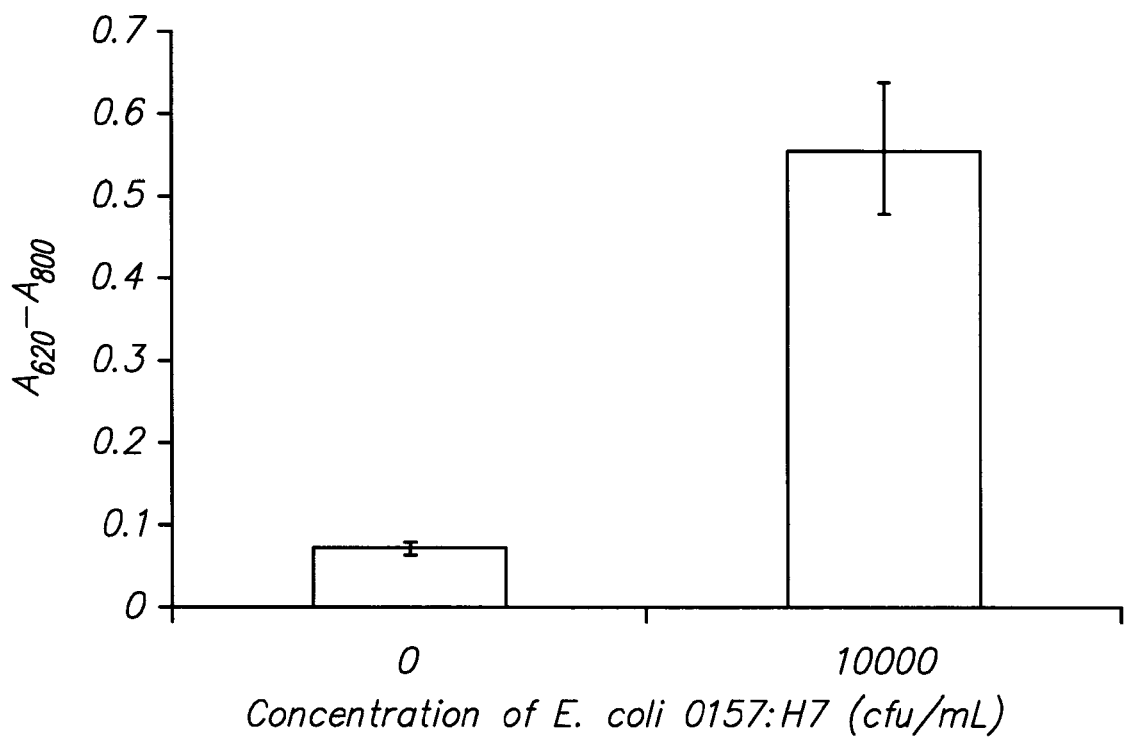
FIG. 15. Result of reproducibility test for the detection of *E. coli* O157:H7 in inoculated ready-to-eat beef lunchmeat without enrichment. Number of blanks: 2/test×5 tests=10; Number of samples: 3/test×5 tests=15.
Figure 16:
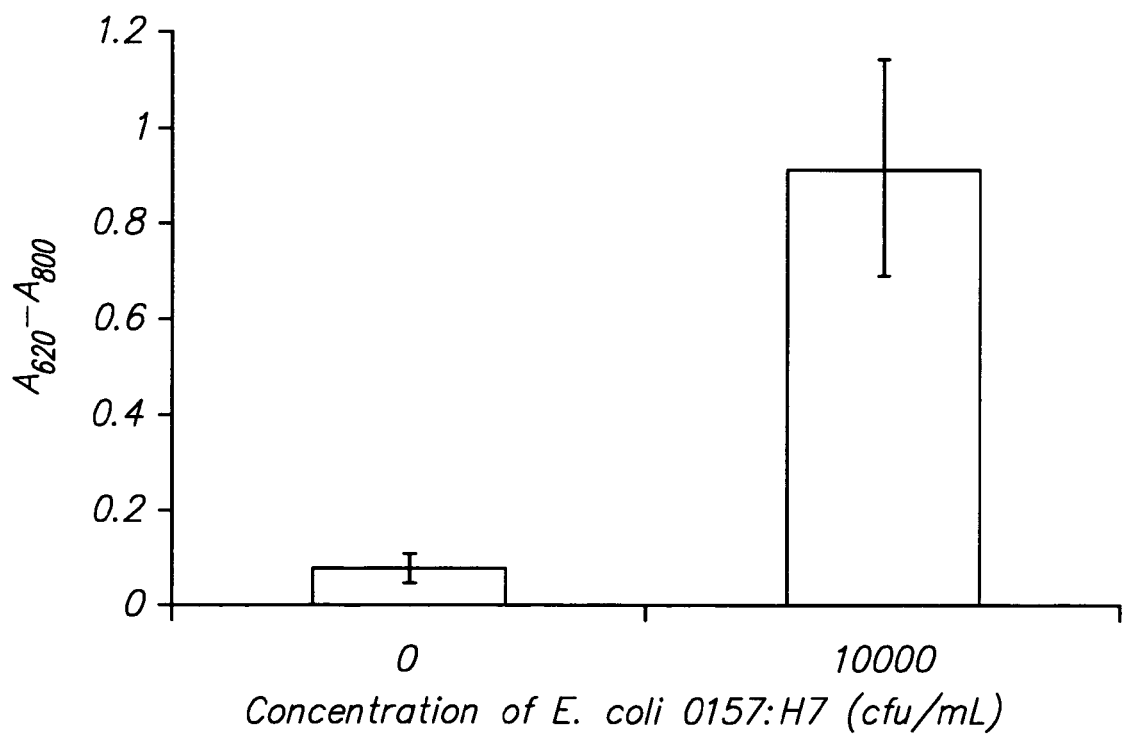
FIG. 16. Result of reproducibility test for the detection of *E. coli* O157:H7 in inoculated ready-to-eat lettuce without enrichment. Number of blanks: 2/test×5 tests=10; Number of samples: 3/test×5 tests=15.
Figure 17:
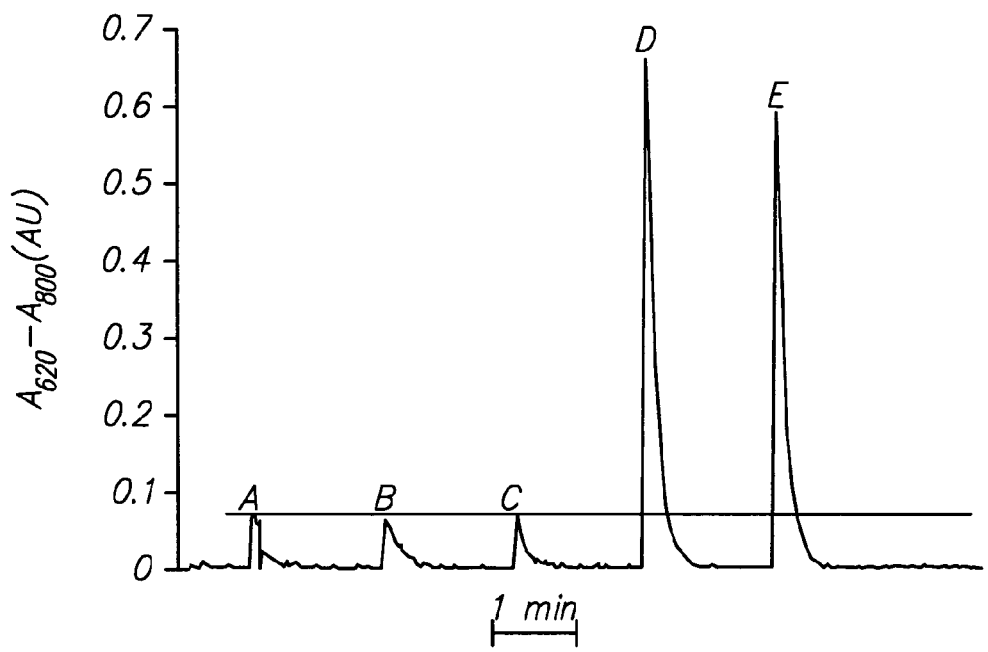
FIG. 17. Result of specificity test for the detection of *E. coli* O157:H7 without enrichment. A, PBS; B, $10^5$ CFU/mL of *L. monocytogenes*; C, $10^5$ CFU/mL of *S. Typhimurium*; D, $10^5$ CFU/mL of *E. coli* O157:H7; E, mixture of the three organisms with a final concentration of $10^5$ CFU/mL for each.

The software's main interface is shown in FIG. 6. The software is composed of task editor, spectral acquisition, kinetic measurement, and other basic I/O (input and output) blocks. The function of task editor is to open/save, check, customize, and run a task. Many user instructions are predefined as normal instructions that can be called and assembled flexibly in the task editor to form a specific task for a particular experiment. The predefined user instructions include those for controlling valves, peristaltic pump, and spectrometer, etc. When the check button on the task editor is clicked, the software will check for syntax errors. After this, the user can click the run button to start a predefined task.

Principle

The multichannel capillary biosensor system is based on the use of capillary/microfluidic sensing channels. Compared with other configurations, the capillary/microfluidic geometry has improved assay kinetics due to the higher surface-to-volume ratio and restricted diffusion of reacting compounds. In addition, capillaries/microfluidics are more suitable for automation, and the consumption of immunoreagents is minimized due to their small dimensions.

Briefly, different samples and reagents are delivered into the sensing channels in a specific sequence. A cleaning step is conducted between the introduction of any two different reagents or samples through two bypass channels to eliminate cross contaminations and/or non-specific bindings. The sensing elements immobilized on the inner surface of the sensing channels, the target analytes in the samples, and labeling agents react in the sensing channels to form sandwich complexes. After rinsing any non-specific bindings with a washing agent, a substrate is introduced and the product is detected. The detection is converted to a direct measurement of a quantity of the analyte in a sample. Multiple analytes and/or samples can be analyzed in one cycle. False positive results are minimized by using specific sensing elements and appropriate blocking, washing, and surface modification.

Optimization of Operating Parameters

The system operating parameters have been optimized extensively for the detection of food pathogens, which involves the quantitation of sandwich immunocomplexes of capture antibodies, target bacteria, and alkaline phosphatase (ALP) labeled-antibodies that are formed in capillary columns. The quantity of ALP conjugates is proportional to the bacterial concentration. Both optical and electrochemical detection modes have been evaluated. In optical measurement, p-nitrophenyl phosphate (pNPP) or 5-bromo-4-chloro-3-indolyl phosphate (BCIP) is used as a substrate of ALP conjugates. It was shown that, for the detection of ALP-Abs in a wide range (1-9 ng/mL), the slope of the calibration curve obtained with BCIP was approximately 2.6 times that obtained with pNPP. More attractively, the result for the detection of ALP-Abs at low levels demonstrated that the background level and the detection limit obtained with BCIP (0.04 AU, 0.2 ng/mL) were both much lower than those obtained with pNPP (0.1 AU, 1 ng/mL). BCIP and pNPP were further compared for the detection of $E. coli$ O157:H7, which was based on the detection of ALP conjugates. The detection signals obtained with BCIP are more discriminating among different cell concentrations. Hence, BCIP was chosen as the ALP substrate for optical measurement.

In addition, 1-naphthyl phosphate (NP) was used as a substrate for electrochemical measurement of the ALP conjugates. Under the catalysis of ALP conjugates, NP is hydrolyzed to naphthol, which showed an anodic current peak at 0.16-0.4 V vs Ag/AgCl. At 0.4 V, the peak current (I) in nA increased linearly with naphthol concentration (C) in the range of 0.05 to 1 μM, the regression equation was I=133.23C+19.36 ($R^2$=0.99), and the relative standard deviations were 0.5~6.2%. Using NP as the substrate, the detection limit for ALP labeled-Abs was as low as 5~50 pg/mL, which was much lower than that obtained with the optical detection modes. However, the electrode was fouled at >100 μM naphthol due to the oxidation of naphthol. Although mechanical polishing, or rinsing with ethanol, water, and scratching with wetted tissues successively could clean the fouled electrode, this cleaning approach is unsuitable for continuous measurement. Therefore, the BCIP-optical detection mode was employed for the development of the biosensor system.

Effects of the operating parameters including sample volume and the reaction time for sample, ALP-Ab, substrate on the detection sensitivity were investigated substantially by means of the fractional factorial design. The optimized parameters were found to be: 0.5-2.0 mL for sample volume, 10-30 min (depending on the target of the detection) for sample reaction time, 10-20 min for enzyme-labeled antibody reaction time, and 5-10 min for substrate reaction time. The total sample testing cycle time was controlled to be approximately 1-2 h per 5 samples.

The well-established ATES-GD approach was used for antibody immobilization, i.e., the inner surface of a silica capillary column was silanized with 3-(aminopropyl) tri-ethoxysilane (ATES) followed by treatment with a linker such as glutaraldehyde (GD), and then the antibody was immobilized via covalent binding. In addition, two other immobilization methods were investigated for preparing antibody-modified capillary columns: one was based on the use of protein A, while the other was based on the use of protein G, both having natural affinity to the Fc region of IgG molecules. No significant difference was observed among the three types of antibody-modified columns in the detection of $E. coli$ O157:H7, and the ATES-GD method was chosen for Ab modification. Long-term stability tests showed that when antibody-modified capillary columns were stored at 4° C., bioactivity could be retained for at least 6 months.

Minimization of False Outcomes

False outcomes, particularly false positives caused by cross-contaminations and/or non-specific bindings, are a common problem encountered in immunoassays. The system configuration and operating parameters have been optimized so as to reduce false-positive outcomes.

The optimal configuration for the multichannel biosensor system is: two bypass channels (1310 and 1610) are used for system cleaning and a low-pulse peristaltic pump is set behind the flow cell. Only after the enzyme substrate is incubated in the capillary column for a determined time, does the pump pull the enzymatic product solution flowing through the detection cell for absorbance measurement. In all other procedures, the pump draws the sample or reagents through the capillary columns directly to the waste vessel via the bypass channel 1610. System cleaning is conducted between the introduction of any two different reagents or samples via the bypass channels 1310 and 1610 to avoid sample-to-sample and/or channel-to-channel cross-contaminations.

In addition to the optimization of system configurations, blocking and washing steps have been optimized to minimize non-specific binding. Different tubing, with or without 1% bovine serum albumin (BSA)-PBS blocked, was compared to check for non-specific binding of enzyme-labeled Abs. Blocked with 1% BSA for one hour, the non-specific bindings on antibody-modified silica capillary columns, PTFE tubing, and Teflon FEP tubing was reduced by approximately 3 fold. Hence, antibody-modified capillary columns as well as flowing/connecting tubing should always be blocked with BSA before use. It was also found that a washing solution, which contained 2 mM imidazole buffered saline with 0.02% Tween 20, was more effective than PBS for rinsing off non-specific binding of enzyme-labeled Abs.

The following examples, which include preferred embodiments, will serve to illustrate the practice of the invention, it being understood that the particulars shown are by way of example and for purpose of illustrative discussion of preferred embodiments of the invention.

Example 1

System Configuration

FIG. 1 shows the system configuration of a preferred embodiment of the biosensor system for the detection of bacteria, proteins, and pesticides. The biosensor system comprises: a multi-position valve (1100) for the selection of a sample or a reagent connected to a multi-channel valve (1300) accommodating five sensing channels for multi-sample/analyte analysis and a first bypass channel (1310) for cleaning purposes; the multi-channel valve being connected to a two-position directing valve (1500), with a first position being connected to a second bypass channel (1610), and a second position being connected to an optical detector (1620) for absorbance measurement; a peristaltic pump (1700) for aspirating the output from the directing valve from either the second bypass channel or the detector to a waste vessel (1800); and a control board (1900) for controlling the system. It has been found that the bypass channels 1310 and 1620 may be important to reduce false-positive. Omitting the bypass channels 1310 and 1620 results in increased false-positive background. The biosensing channels 1320-1360 are antibody- or antigen-modified silica capillary columns, preferably with an inner diameter of 250 μm and a length of 25 cm. Other flow tubing have an inner diameter of 250 μm or 500 μm. This preferred biosensor system can test up to five samples in one cycle and the sample throughput is higher than that of the single-channel system by more than 2-3 times without significant increase in the instrument cost. Another attractive feature is that it can run both positive and negative controls along with the samples and therefore provide more reliable results.

While bacteria, proteins, and pesticides are the preferred embodiment of the analyte, it will be understood that the analyte encompasses microorganisms (including bacteria, viruses, fungi, etc.), macromolecules (including proteins, enzymes, DNA, RNA, polysaccharides, liposomes, glycosides, etc) and small molecules (including pesticides, drugs, explosives, etc.).

While antibody- and antigen-modified silica capillary columns with an inner diameter of 250 μm and a length of 25 cm are the preferred embodiment of the sensing channels (1320-1360), it will be understood that the sensing channels encompass capillary columns and microfluidic chips of any material (including glass, ceramic, polymer, metal, etc.) that are modified with a sensing element selected from the group consisting of antibodies, antigens, single-stranded DNA, RNA, natural receptors, and synthetic receptors. The inner diameter of the sensing channels is preferably about 10 μm-1 mm, more preferably 200-300 μm, and most preferably 250 μm. The length diameter of the sensing channels is preferably about 5 cm-3 m, more preferably 10-50 cm, and most preferably 25 cm.

While the multi-position valve (1100) is the preferred embodiment of the selecting valve system for selection of a sample or reagent, it will be understood that the device encompasses any of a variety of configurations so long as the selecting valve system has at least two positions. The selecting valve system also encompasses multiple single position valves.

While the multi-channel valve (1300) is the preferred embodiment of the second valve system, it will be understood that the evidence encompasses any of a variety of configurations so long as the second valve system accommodates at least one sensing channel. The second valve system also encompasses multiple single-channel valves.

While the two-position directing valve (1500) is the preferred embodiment of the directing valve system, it will be understood that the evidence encompasses any of a variety of configurations so long as the directing valve system has at least two positions. The directing valve system also encompasses multiple single-position valves.

While the optical absorbance detector (1620) is the preferred embodiment of the detector, it will be understood that the evidence encompasses any of a variety of configurations so long as the detector measures optically (including absorbance, fluorescence, chemiluminescence, etc) or electrochemically (including current, potential, impedance, conductivity, capacitance, etc). The detector also encompasses a combination of two or more different detectors.

While the peristaltic pump (1700) is the preferred embodiment of the pump for moving the sample or a reagent, it will be understood that the evidence encompasses any of a variety of configurations so long as the pump moves the sample or a reagent continuously or discontinuously. The pump also encompasses solenoid pumps, syringe pump, vacuum pumps, piezoelectric pumps, etc. The pump can be placed at either the downstream or the upstream of the sensing channels.

Example 2

Detection of *E. coli* O157:H7

*E. coli* O157:H7 is used as a model analyte to demonstrate the application of the biosensor system to detect microorganisms. Anti-*E. coli* O157:H7 antibody-modified capillary columns are used as the biosensing channels 1320-1360. Briefly, samples and reagents are delivered into individual sensing channels in the following sequence: sample solution→washing solution→enzyme-labeled anti-*E. coli* O157:H7 antibody solution→washing solution→substrate solution. A cleaning step is conducted between the introduction of any two different reagents or samples through the bypass channel to eliminate cross contaminations and/or non-specific bindings. The immobilized antibodies, *E. coli* O157:H7 cells, and enzyme labeled antibodies react in the capillary columns to form sandwich immunocomplexes. After rinsing any non-specific bindings with the washing solution, a substrate (e.g. BCIP) is introduced and the enzymatic product is followed by measuring optical absorbance. Under catalysis of the enzyme conjugates, BCIP is hydrolyzed to yield a soluble blue product that has a maximum absorbance at 600-620 nm. The signal intensity is correlated to the initial concentration of *E. coli* O157:H7 in a sample.

FIGS. 7-17 show results of the biosensor system for the detection of *E. coli* O157:H7 in PBS and food samples including milk, ready-to-eat lettuce and lunchmeat. It has been shown that the biosensor system is able to analyze up to five samples per batch in 1-2 h with a detection limit down to 100 cfu/mL without enrichment or less than 1 cfu/mL with 5-6 h enrichment. Other bacteria do not interfere with the detection of *E. coli* O157:H7. The sample-to-sample and batch-to-batch variations are generally smaller than 10% RSD.

Example 3

Detection of Vinculin

Vinculin, a protein with a molecular weight of 116 kDa, is used as a model analyte to demonstrate the application of the biosensor system to detect macromolecules. Anti-viculin antibody-modified capillary columns are used as the biosensing channels 1320-1360. Briefly, samples and reagents are delivered into individual sensing channels in the following sequence: sample solution→washing solution→enzyme-labeled anti-vinculin antibody solution→washing solution→substrate solution. A cleaning step is conducted between the introduction of any two different reagents or samples through the bypass channel to eliminate cross contaminations and/or non-specific bindings. The immobilized antibodies, vinculin molecules, and enzyme labeled antibodies react in the capillary columns to form sandwich immunocomplexes. After rinsing any non-specific bindings with the washing solution, a substrate (e.g. BCIP) is introduced and the enzymatic product is followed by measuring optical absorbance. Under catalysis of the enzyme conjugates, BCIP is hydrolyzed to yield a soluble blue product that has a maximum absorbance at 600-620 nm. The signal intensity is correlated to the initial concentration of vinculin in a sample.

Figure 18:
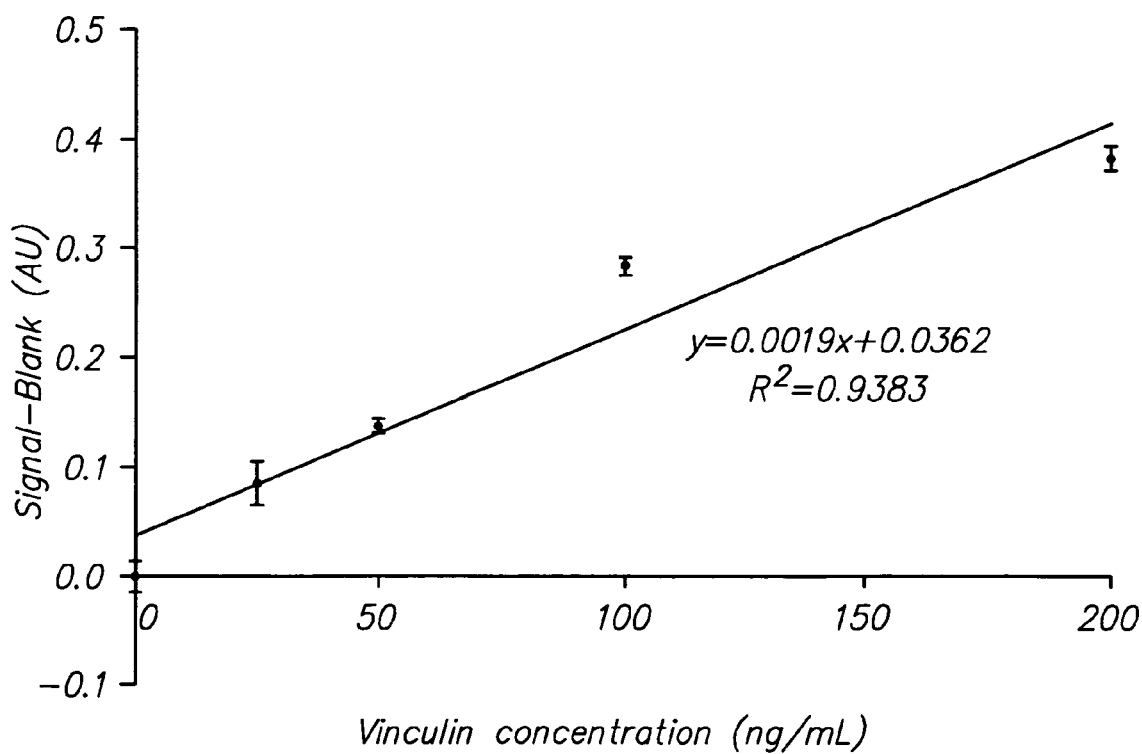
FIG. 18. Result of the biosensor system for the detection of vinculin showing a linear detection range of 25-200 ng/mL (0.22-1.72 nM) and a detection limit of 4.6 ng/mL (40 pM) at S/N=3.
Figure 19:
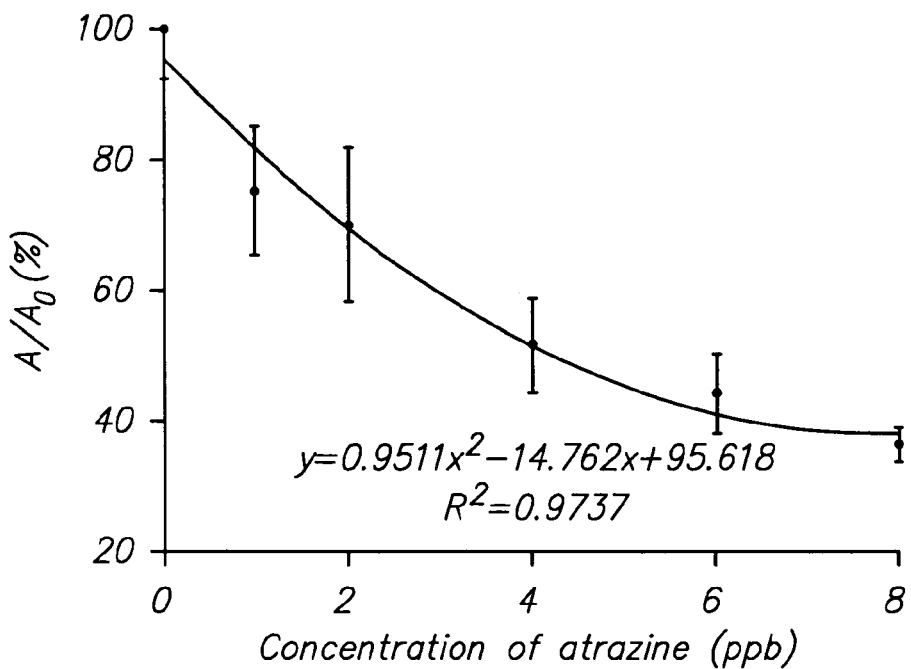
FIG. 19. Result of the biosensor system for the detection of atrazine at low concentrations. A/A0 represents the ratio of absorbance in the presence of atrazine (sample absorbance) over absorbance in the absence of atrazine (blank absorbance). Anti-atrazine concentration: 1:1000 dilution.
Figure 20:
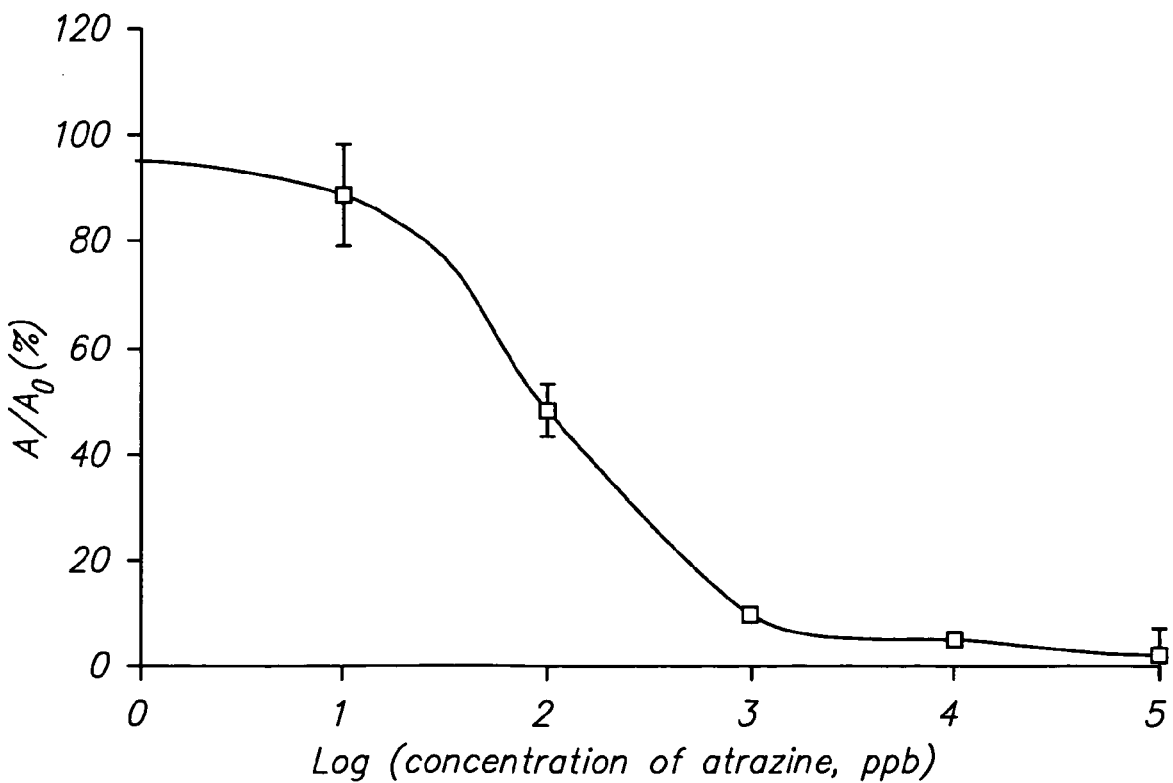
FIG. 20. Result of the biosensor system for the detection of atrazine at high concentrations. Anti-atrazine concentration: 1:250 dilution.
Figure 21:
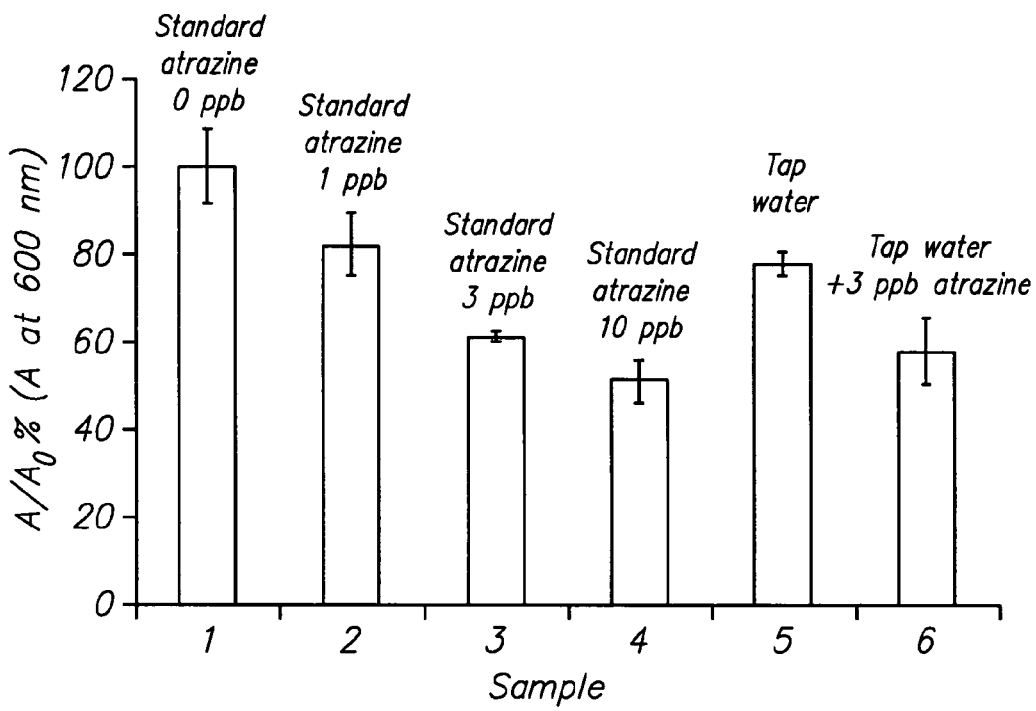
FIG. 21. Result of the biosensor system for the detection of atrazine in tap water.
Figure 22:
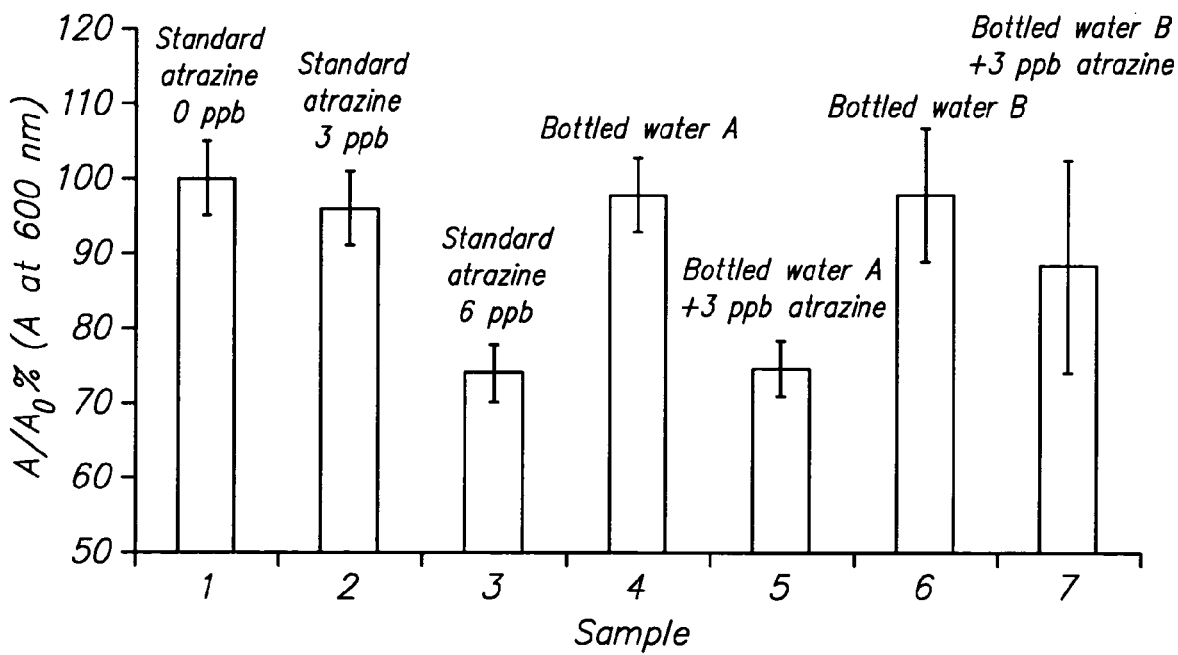
FIG. 22. Result of the biosensor system for the detection of atrazine in bottled water.
Figure 23:
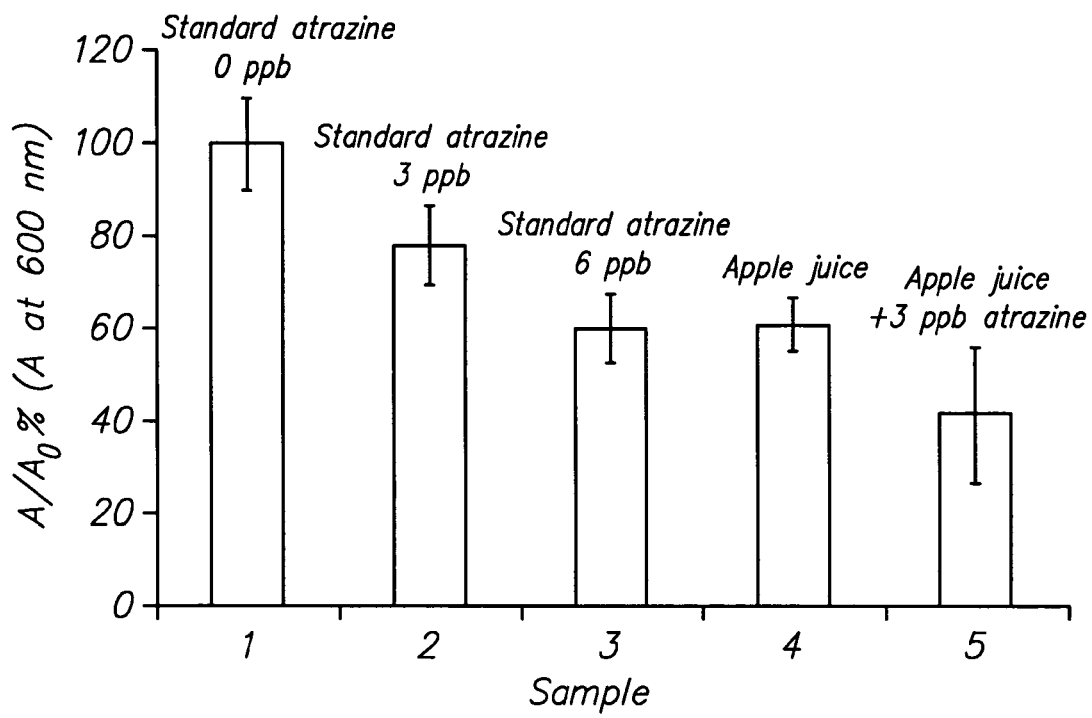
FIG. 23. Result of the biosensor system for the detection of atrazine in apple juice.
Figure 24:
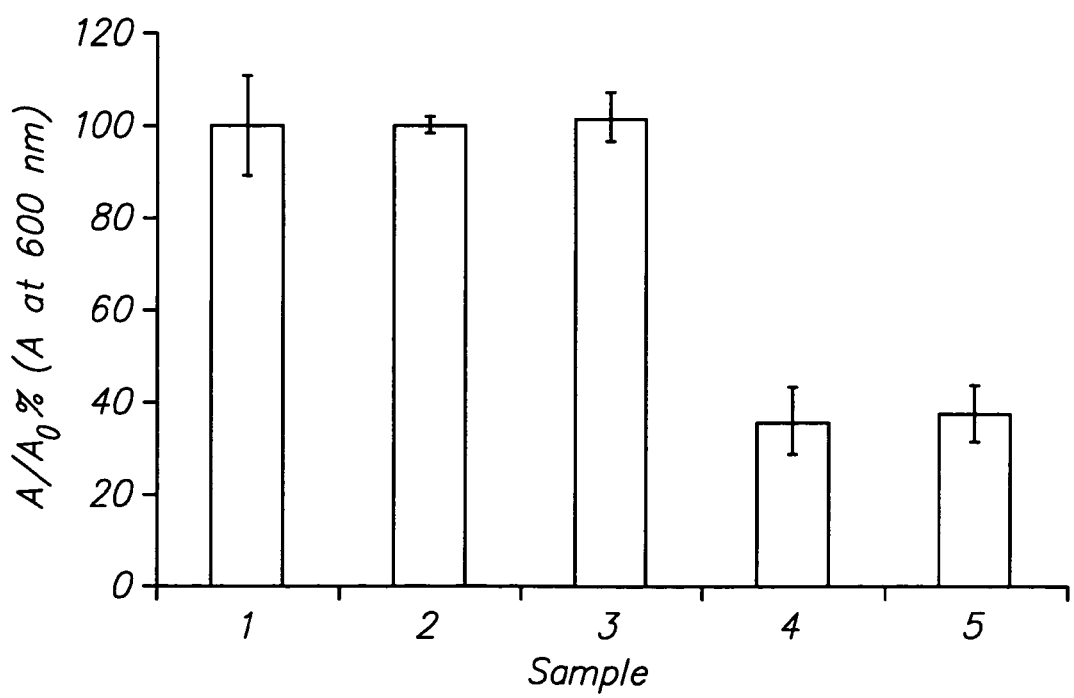
FIG. 24. Result of specificity test for the detection of atrazine. 1: blank (no atrazine); 2: 10 ppb desethyl atrazine; 3: 1 ppm chlorpyrifos; 4: 10 ppb atrazine; 5: mixture of 10 ppb atrazine+10 ppb desethyl atrazine+1 ppm chlorpyrifos.

FIG. 18 shows the result of the biosensor instrument for the detection of vinculin. It has been shown that the biosensor system offers a linear detection range of 25-200 ng/mL (0.22-1.72 nM). The assay precision is 3-23%, and the lower limit of detection (LOD) is 4.6 ng/mL (40 pM) at a signal-to-noise ratio of 3. The detection limit is close to the theoretical LOD (10-100 pM) for a non-competitive immunoassay with a typical antibody-antigen affinity constant of $K=10^8-10^9$ $M^{-1}$ and 10% CV (coefficient of variation or relative error) on a 1% non-specific signal (NSS) according to the model LOD=NSS×CV/K. The biosensor is more sensitive than conventional ELISA by one order of magnitude in terms of LOD and the biosensor sensitivity is suitable for detection of vinculin in broiler lymphocyte samples when appropriately diluted.

Example 4

Detection of Atrazine

Atrazine, a pesticide chemical with a molecular weight of 216 Da, is used as a model analyte to demonstrate the application of the biosensor system to detect small molecules. BSA-atrazine conjugate-modified capillary columns are used as the biosensing channels 1320-1360. Briefly, a certain amount of monoclonal anti-atrazine antibodies are added to samples. The mixtures are delivered into the sensing channels, wherein the atrazine molecules in the samples and the conjugated atrazine molecules on the inner surface of sensing channels competed for the same antibodies. This is followed by the introduction of enzyme labeled anti-IgG and the substrate BCIP in sequence. The concentration of atrazine was determined by measuring the absorbance of the enzymatic product at 600 nm: the higher concentration of atrazine in the sample, the lower optical absorbance of the product solution.

FIGS. 19-24 shows some results of the biosensor system for the detection of atrazine. It has been shown that the detection limit is at least 1 ppb, exceeding that required by the EPA for atrazine residues in drinking water (3 ppb). In the detection of 10 ppb atrazine, no significant interference is observed from desethyl atrazine, one atrazine degradation product, at the same level (10 ppb) or from chlorpyrifos, another widely used pesticide, even at an extremely high level (1 ppm). The biosensor system has been successfully applied to determine atrazine in tap water, bottled water, and apple juice.

The invention claimed is:

1. A device for detection of an analyte in a sample comprising: a multi-position selecting valve system for selection between one of the sample and at least one reagent, wherein the multi-position selecting valve system is fluidically connected to a second valve system accommodating at least two sensing channels each comprising a capillary column and a first bypass channel separate from the sensing channels; the second valve system being connected to a detector for detecting the analyte; a control system for controlling the position of the multi-position selecting valve system and the second valve system; and a directing valve system fluidically connected between the second valve system and the detector, the directing valve system having at least two positions, with a first position being connected to a second bypass channel and a second position being connected to the detector, wherein the second bypass channel is not fluidically connected to the detector, and further wherein the control system is further configured to control the directing valve system.

2. The device of claim 1 further comprises a pump connected at one end to the detector and at a second end to a waste vessel.

3. The device of claim 1 wherein the analyte is selected from the group consisting of microorganisms, macromolecules, and small molecules.

4. The device of claim 1 wherein the detector detects optically or electrochemically.

5. The device of claim 1 wherein the detection is converted to a direct measurement of a quantity of the analyte in the sample.

6. The device of claim 1 wherein at least one of the sensing channels is modified with a sensing element selected from the group consisting of antibodies, antigens, single-stranded DNA, RNA, natural receptors, and synthetic receptors.

7. The device of claim 1 wherein at least one of the sensing channels has an inner diameter of about 10 μm-1 mm.

8. The device of claim 1 wherein at least one of the sensing channels has an inner diameter of about 200 μm-300 μm.

9. The device of claim 1 wherein at least one of the sensing channels has an inner diameter of about 250 μm.

10. The device of claim 1 wherein at least one of the sensing channels has a length of about 5 cm-3 m.

11. The device of claim 1 wherein at least one of the sensing channels has a length of about 10-50 cm.

12. The device of claim 1 wherein at least one of the sensing channels has a length of about 25 cm.

13. A device for detection of an analyte in a sample comprising: a multi-position selecting valve system for selection between one of the sample and at least one reagent, wherein the multi-position selecting valve system is fluidically connected to one of at least two sensing channels each comprising a capillary column; the one of the at least two sensing channels being connected to a detector for detecting the analyte; a control system for controlling the position of the multi-position selecting valve system; and a directing valve system fluidically connected between at least one of the at least two sensing channels and the detector, the directing valve having at least two positions, with a first position being connected to a second bypass channel and a second position being connected to the detector, wherein the second bypass channel is not fluidically connected to the detector, and further wherein the control system is further configured to control the directing valve system.

14. The device of claim 13 further comprises a pump connected at one end to the second bypass channel and the detector and at a second end to a waste vessel.

* * * * *